United States Patent [19]

Orfeo et al.

[11] Patent Number: 5,043,519

[45] Date of Patent: Aug. 27, 1991

[54] PROCESS FOR THE PRODUCTION OF TERTIARY OLEFINS BY DECOMPOSITION OF ALKYL-TERT.-ALKYL-ETHERS

[75] Inventors: Forlani Orfeo, Milan; Piccoli Valerio, Monza; Notari Bruno, S. Donato Milanese, all of Italy

[73] Assignee: Snamprogetti S.p.A., Milan, Italy

[21] Appl. No.: 449,468

[22] Filed: Dec. 12, 1989

Related U.S. Application Data

[63] Continuation of Ser. No. 337,337, Apr. 13, 1989, abandoned, which is a continuation of Ser. No. 26,909, Feb. 27, 1987, abandoned.

[30] Foreign Application Priority Data

Jul. 5, 1985 [IT] Italy .............................. 21450 A/85

[51] Int. Cl.$^5$ ................................................ C07C 1/24

[52] U.S. Cl. ..................................................... 585/640
[58] Field of Search ......................................... 585/640

[56] References Cited

U.S. PATENT DOCUMENTS 4,254,296  3/1981  Manera et al. ...................... 585/640

*Primary Examiner*—Curtis R. Davis
*Attorney, Agent, or Firm*—Hedman, Gibson, Costigan & Hoare

[57] ABSTRACT

A process for the production of tertiary olefins by means of the decomposition of the corresponding alkyl-tert.alkyl-ethers, by reacting said alkyl-tert.alkyl-ethers in the presence of a catalyst constituted by silica modified by the addition of alumina in an amount comprised within the range of from 0.1 to 1.5% by weight relatively to the silica.

1 Claim, 1 Drawing Sheet

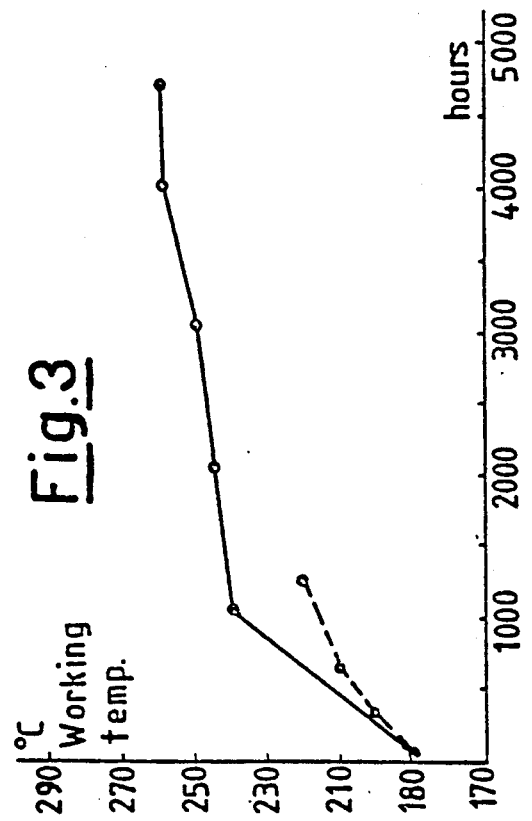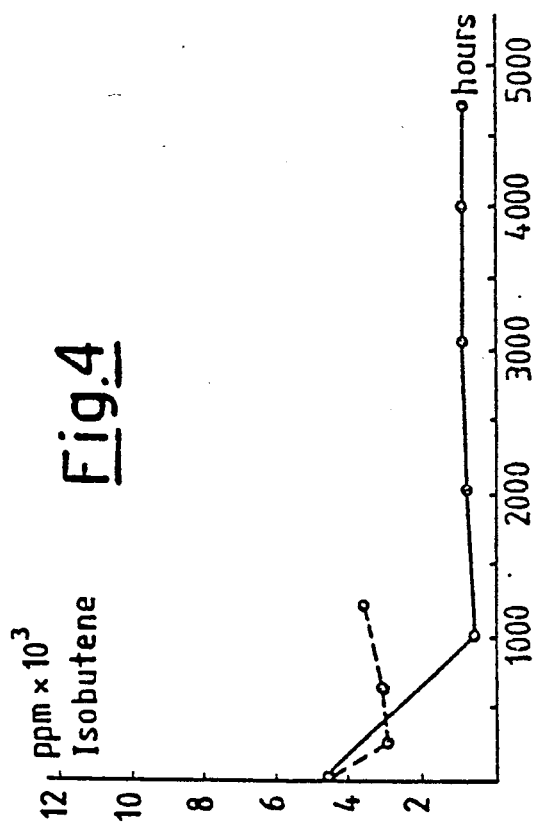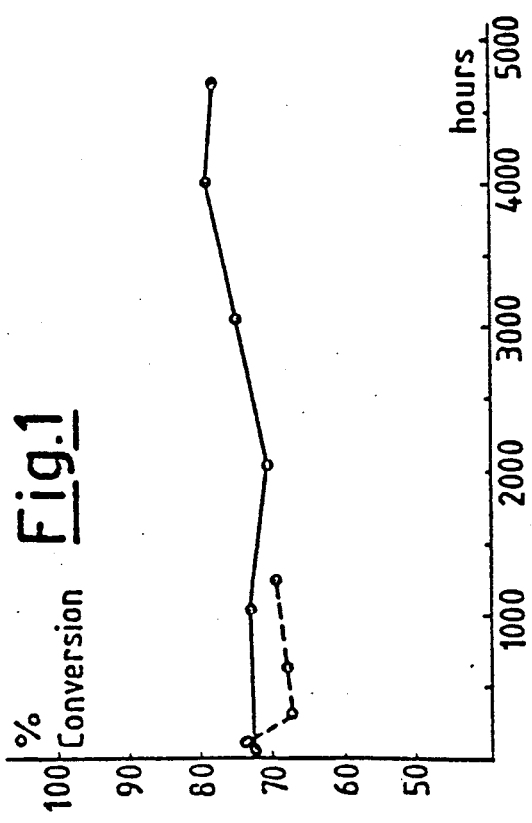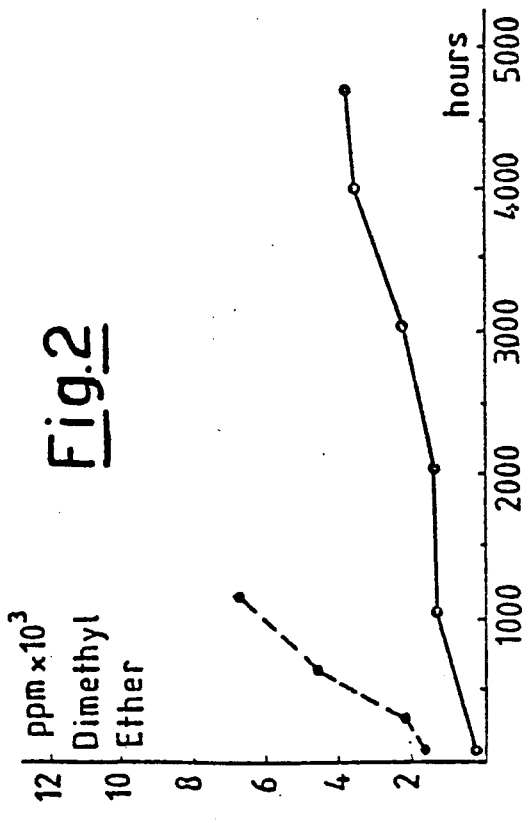

PROCESS FOR THE PRODUCTION OF TERTIARY OLEFINS BY DECOMPOSITION OF ALKYL-TERT.-ALKYL-ETHERS

This application is a continuation of U.S. patent application Ser. No. 07/337,337, filed Apr. 13, 1989, which is a continuation of U.S. patent application Ser. No. 07/026,909, filed Feb. 27, 1987, both of which are now abandoned.

The present invention relates to a process for the production of pure tertiary olefins, by the decomposition of the corresponding alkyl-tert.alkyl-ethers.

Several methods are known for the obtainment of tertiary olefins.

For example, some of such methods are based on the use of $H_2SO_4$ which however, besides the corrosion and pollution problems, show several drawbacks, among which the need for concentrating the acid before recycling it. Other methods are based on the decomposition of the corresponding methyl-ethers in the presence of suitable catalytic systems.

However, the use of the herein mentioned catalysts causes, in the most of the cases, the formation of dialkyl-ethers due to the dehydration of the corresponding primary alcohols.

The higher the operating temperature, the more easily this reaction occurs; some of the catalysts of the prior art require rather high temperatures to be used, which leads to a loss of alcohol, with the consequent need for further alcohol to be fed to the initial etherification reaction.

Furthermore, the formation of dialkylether requires a greater complexity at the level of reaction facilities, because e separation of the dialkyl ether from the tertiary olefin becomes necessary. And still furthermore, the formation of a considerable amount of dialkyl-ether renders necessary also the primary alcohol to be hydrated before being recycled, otherwise in the etherification reaction phase separation and possibility of formation of tertiary alcohols would occur.

A further drawback, to be faced when the reaction is carried out beyond certain temperature limits is given by the occurrence of dimerization and trimerization of the tertiary olefin recovered from the decomposition of the ethers.

Some drawbacks are overcome when the reaction of decomposition of the tert.alkyl ethers is carried out in the presence of a catalytic system constituted by activated alumina modified by the partial substitution of superficial —OH groups with silanol groups, according to as disclosed in Italian patents Nos. 1,001,614 and 1,017,878, in the name of the present Applicant.

Unfortunately, the activated alumina modified according to as disclosed in the above mentioned patents causes, already in case of a small increase in reaction temperature, the formation of dialkyl-ether, with the consequent reduction of the recovery of the primary alcohol to be recycled.

In the U.S. Pat. No. 4,254,296 always in the name of the same Applicant, to the contrary, a catalyst is used, selected among a crystalline silica modified with oxides of metal cations, such as aluminium and boron, by which much higher performances are achieved than by the activated alumina modified by silanolic groups.

Such a material has however an extremely high production cost, and is difficult to prepare.

Furthermore, the catalyst constituted by silicized alumina does not have a long life, because it does not succeed in limiting the side products within such limits as to allow financially interesting quantitative recoveries of the products obtained. Greater amounts of dimethyl-ether correspond to greater amounts of pure methanol, and to greater amounts of isobutene going lost during the distillation and separation step.

We have surprisingly found that it is possible to overcome the drawbacks of the prior art by using a catalyst which, besides having a low cost and being simple to prepare, has good catalytic performance.

The process of the present invention for the production of tertiary olefins consists of reacting the corresponding alkyl-tert.alkyl-ethers in the presence of a catalyst comprising silica modified by the addition of alumina in an amount comprised within the range of from 0.1 to 1.5% by weight relative to the silica.

In particular, said process can be used for the purpose of obtaining isobutene from the breakage of methyl-tert.-butyl-ether.

The reaction of decomposition of the alkyl-tert.alkyl-ethers is carried out at temperatures equal to or lower than 500° C., preferably within a range of from 130° to 350° C.

The reaction is generally carried out under pressures comprised within the range of from 1 to 10 $kg/cm^2$, preferably under a pressure at least equal to the vapour pressure of the olefin to be recovered at the condensation temperature provided.

The space speed expressed as the volume of liquid per volume of catalyst per hour (LHSV), at which the reaction is carried out, is comprised within the range of from 0.5 to 200 $h^{-1}$, preferably of from 1 to 50 $h^{-1}$.

The catalyst can be simply prepared by starting from a preformed silica having the necessary purity (which is a product available from the market), then limiting the operations to the impregnation, drying and calcination. The impregnation is carried out with a solution of a salt of aluminium (for example, a nitrate or an isopropoxide), so to give the desired end content of alumina.

The primary alcohols which can be recovered at the end of the decomposition process of the invention contain preferably from 1 to 6 carbon atoms.

The process of the present invention can be used for recovering the tertiary olefins from mixtures of olefins from $C_4$ to $C_7$ such as, for example, those outcoming from thermal cracking, steam cracking or cat cracking.

Among the various tertiary olefins which can be obtained in the pure state, isobutylene, isoamylenes such as 2-methyl-2-butene and 2-methyl-1-butene, isohexenes, such as 2,3-dimethyl-1-butene, 2,3-dimethyl-2-butene, 2-methyl-1-pentene, 2-methyl-2-pentene, (cis and trans) 3-methyl-2-pentene, 2-ethyl-1-butene and 1-methyl-cyclopentene, or finally the tertiary isoheptenes.

The conversion of the tert.alkyl ether into primary alcohol or tertiary olefin is practically quantitative.

The formation is observed of very minor amounts of dimers and trimers of the tertiary olefin recovered, while no tertiary alcohol is formed.

The operating modalities and the advantages of the process according to the present invention shall be more evident from the examination of the following illustrative Examples, by which however the invention is not to be considered as being limited.

EXAMPLE 1

This Example illustrates the different behaviour of silica modified with alumina relative to a catalyst of the prior art: alumina stabilized with silica.

The catalyst constituted by silica modified with alumina has been prepared as follows:

10 g of high-purity silica, which will be denominated as "Silica A", having the following composition:

$Na_2O$: 0.05% by weight
$SO_4$: 0.15% by weight
$Al_2O_3$: 0.30% by weight
$SiO_2$: balance to 100, is treated with an aqueous solution containing 0.368 g of aluminum nitrate (added $Al_2O_3 = 0.5\%$ by weight relative to the silica).

The material obtained is slowly dried at 120° C. for three hours, and is then calcined at 500° C. for 4 hours.

At FIGS. 1, 2, 3 and 4, the performance is reported of the catalyst used in the process of decomposition of methyl-tert.butyl-ether, and of the catalyst of the prior art hereinabove mentioned.

The charts of FIGS. 1, 2, 3 and 4 have on the abscissae the running hours, and on the ordinates: the chart of FIG. 1, the percent conversion of methyl-tert.butyl-ether; the chart of FIG. 2, the ppm of dimethyl-ether produced; the chart of FIG. 3, the operating temperature (as °C.) to get the conversion as indicated; and the chart of FIG. 4, the ppm of diisobutylene produced. The alumina stabilized by silica is shown in broken line, the silica modified with alumina in continuous line.

It can be observed from the charts how prolonging the life of the catalyst of the present patent application is possible by keeping the temperature at nearly constant values (after the initial stabilization), with the conversion being maintained constant, and the formation of by-products being maintained within acceptable limits.

EXAMPLE 2

This Example shows the performance of commercial silicas, and of silicas modified with alumina.

In following Table 1, the percent conversions of methyl-tert.butyl-ether are compared by using:

the commercial silica (Silica A) of Example 1, in the same amount;

the silica modified by the addition of alumina, always in the same amount as of Example 1;

the commercial silica (which will be denominated "Silica B"), in the amount of 10 g, having the following composition:

$Na_2O$: 0.12% by weight
$SO_4$: 0.35% by weight
$Al_2O_3$: 0.12% by weight
$SiO_2$: balance to 100;

the silica modified, by starting from silica B, by 0.368 g of aluminum nitrate (added $Al_2O_3 = 0.5\%$ by weight relatively to the silica), prepared as described in Example 1.

TABLE 1

CRACKING OF MTBE
Comparison of Activity of Two Silicas Having
Different Purity Levels
Temperature = 180° C. LHSV = 2

| | MTBE % Conversion | |
|---|---|---|
| | After 1 Reaction hour | After 6 Reaction hours |
| Silica A as such | 99.0 | — |
| Silica B as such | 30.0 | — |
| Silica A + $Al_2O_3$ 0.5% | 99.0 | 99.0 |
| Silica B + $Al_2O_3$ 0.5% | 92.0 | 80.0 |

The addition of 0.5% of $Al_2O_3$ to silica is necessary to make the activity of the catalyst, which otherwise would drop very rapidly, stable over time.

EXAMPLE 3

One of the limiting factors of the reaction is the formation of dimethyl-ether, due to the methanol dehydration reaction. As it appears from FIG. 1 of Example 1, the reaction with the catalyst comprising silicized alumina has been discontinued after about 1000 hours, because of the excessive formation of dimethyl-ether (see FIG. 2), which leads to a net loss in methanol recovery, and to a loss of isobutene from the head of the column of separation of the same dimethyl-ether.

It has been found now that, by adding water to the MTBE reacted, the methanol-dimethylether equilibrium is shifted backwards, with a consequent increase of methanol recovery.

The data obtained is reported in Table 2.

TABLE 2

DECOMPOSITION OF MTBE
Influence of the Presence of Water in the Reaction Charge
T = 260° C. LHSV = 2 $h^{-1}$ P = 6 $kg/cm^2$

| Running hours | % of $H_2O$ in charge | % Conversion of MTBE | ppm of DME in products | % Recovery of $CH_3OH$ |
|---|---|---|---|---|
| 5552 | traces | 76.77 | 4550 | 97.65 |
| 5744 | 0.3 | 76.55 | 3240 | 98.30 |
| 5912 | 0.5 | 76.85 | 2970 | 98.50 |
| 6152 | 1.2 | 74.62 | 1870 | 99.00 |
| 6200 | 1.2 | 75.68 | 1780 | 99.06 |

EXAMPLE 4

By using the silica modified with alumina of Example 1, in Table 3 the data is reported which relates to the tests carried out by two different methods, the one with 1.5 cc of catalyst, and the other with 40 cc of catalyst.

TABLE 3

DECOMPOSITION OF MTBE WITH SILICA MODIFIED
WITH ALUMINA AS THE CATALYST

| Running hours | Reactor temperature | % Conversion | ppm of DME | $CH_3OH$ recovery, % by weight | Isobutene recovery, % by weight |
|---|---|---|---|---|---|
| (A) 40-cc Reactor (p = 6 $kg/cm^2$; LHSV = 2) | | | | | |
| 28 | 195° C. | 88.3 | 100 | 99.9 | 98.4 |
| 50 | 195° C. | 77.1 | 100 | 99.9 | 99.5 |
| 509 | 241° C. | 87.9 | 1190 | 99.4 | 99.9 |
| 1000 | 246° C. | 80.8 | 1260 | 99.3 | 99.9 |
| 1500 | 245° C. | 85.1 | 1500 | 99.2 | 99.9 |
| (B) 1.5-cc Reactor (p = 6 $kg/cm^2$; LHSV = 2) | | | | | |
| 22 | 190° C. | 73.5 | 100 | 99.9 | 99.1 |
| 1034 | 240° C. | 72.8 | 1270 | 99.3 | 99.9 |
| 2021 | 245° C. | 70.9 | 1350 | 99.3 | 99.9 |
| 3022 | 250° C. | 75.0 | 2160 | 98.9 | 99.9 |
| 3990 | 260° C. | 79.0 | 3560 | 98.9 | 99.9 |
| 4500 | 260° C. | 77.8 | 4000 | 98.2 | 99.9 |

We claim:

1. A process for producing tertiary olefins comprising: decomposing an alkyl-tertiary alkyl ether in the presence of an alumina-modified silica catalyst at a pressure of 1 to 10 $kg/cm^2$, a temperature of up to 500° C., and a Liquid Hourly Space Velocity of 0.5 to 200 $h^{-1}$, wherein the catalyst has an alumina content of about 0.5% by weight relative to the silica content and is prepared from high purity silica, containing not more than 0.05% by weight $Na_2O$, not more than 0.15% by weight $SO_4$, and not more than 0.30% by weight $Al_2O_3$ initial impurities.

* * * * *